(12) United States Patent
Hart

(10) Patent No.: US 9,427,228 B2
(45) Date of Patent: Aug. 30, 2016

(54) SUTURE CARTRIDGE FOR MENISCAL REPAIR

(71) Applicant: Karl Storz GmbH & Co. KG, Tuttlingen (DE)

(72) Inventor: Rickey Hart, Marco Island, FL (US)

(73) Assignee: Karl Storz GmbH & Co. KG, Tuttlingen (DE)

( * ) Notice: Subject to any disclaimer, the term of this patent is extended or adjusted under 35 U.S.C. 154(b) by 174 days.

(21) Appl. No.: 13/673,525

(22) Filed: Nov. 9, 2012

(65) Prior Publication Data
US 2014/0131249 A1    May 15, 2014

(51) Int. Cl.
*A61B 17/00* (2006.01)
*A61B 17/06* (2006.01)
*A61B 17/04* (2006.01)

(52) U.S. Cl.
CPC ..... *A61B 17/06114* (2013.01); *A61B 17/0401* (2013.01); *A61B 17/06109* (2013.01); *A61B 17/06133* (2013.01); *A61B 2017/0404* (2013.01); *A61B 2017/0409* (2013.01); *A61B 2017/0416* (2013.01); *A61B 2017/0417* (2013.01); *A61B 2017/06142* (2013.01)

(58) Field of Classification Search
CPC .............. A61B 2017/06142; A61B 17/06114; A61B 2017/0416; A61B 2017/06057; A61B 17/04; A61B 17/0401; A61B 17/0485
USPC ....... 206/63.3, 227, 339, 380, 363; 606/148, 606/232
See application file for complete search history.

(56) References Cited

U.S. PATENT DOCUMENTS

| | | | | |
|---|---|---|---|---|
| 3,206,018 A | * | 9/1965 | Lewis et al. | 206/63.3 |
| 4,120,397 A | * | 10/1978 | Neumann | 206/370 |
| 4,899,743 A | * | 2/1990 | Nicholson et al. | 606/139 |
| 4,946,468 A | * | 8/1990 | Li | 606/232 |
| 5,078,730 A | * | 1/1992 | Li et al. | 606/228 |
| 5,174,087 A | * | 12/1992 | Bruno | 53/430 |
| 5,307,924 A | * | 5/1994 | Manosalva et al. | 206/63.3 |
| 5,458,609 A | * | 10/1995 | Gordon et al. | 606/144 |
| 5,478,344 A | * | 12/1995 | Stone et al. | 606/144 |
| 5,478,345 A | * | 12/1995 | Stone | A61B 17/0469 206/339 |
| 5,501,683 A | | 3/1996 | Trott | |
| 5,503,266 A | * | 4/1996 | Kalbfeld et al. | 206/63.3 |
| 5,643,295 A | * | 7/1997 | Yoon | 606/151 |
| 5,669,490 A | * | 9/1997 | Colligan et al. | 206/63.3 |
| 5,675,961 A | * | 10/1997 | Cerwin et al. | 53/430 |

(Continued)

FOREIGN PATENT DOCUMENTS

| | | |
|---|---|---|
| EP | 1588666 A2 | 10/2005 |
| EP | 1818019 A1 | 8/2007 |

OTHER PUBLICATIONS

European Search Report Application No. EP 13 19 1847 Completed: Jan. 29, 2014; Mailing Date: Feb. 21, 2014 8 pages.

*Primary Examiner* — Anthony Stashick
*Assistant Examiner* — Ernesto Grano
(74) *Attorney, Agent, or Firm* — Whitmyer IP Group LLC

(57) ABSTRACT

A cartridge for holding a suture anchor having a body, including a holder assembly adapted to releasably hold at least one suture anchor, the body having a proximal face, a passage extending from the proximal face of the body to the holder assembly, and a spool adapted to releasably wind a portion of a suture therearound is provided. A kit, including at least one suture anchor, a cartridge for holding the at least one suture anchor, and a suture may also be provided.

21 Claims, 14 Drawing Sheets

(56) References Cited

U.S. PATENT DOCUMENTS

| | | | | |
|---|---|---|---|---|
| 5,709,693 A * | 1/1998 | Taylor | | 606/145 |
| 5,715,942 A * | 2/1998 | Li et al. | | 206/339 |
| 5,733,293 A * | 3/1998 | Scirica et al. | | 606/144 |
| 5,733,308 A * | 3/1998 | Daugherty et al. | | 606/232 |
| 5,741,300 A | 4/1998 | Li | | |
| 5,814,069 A * | 9/1998 | Schulze et al. | | 606/228 |
| 5,843,084 A | 12/1998 | Hart et al. | | |
| 5,894,921 A * | 4/1999 | Le et al. | | 206/63.3 |
| 6,016,905 A * | 1/2000 | Gemma et al. | | 206/63.3 |
| 6,080,184 A * | 6/2000 | Peters et al. | | 606/228 |
| 6,126,666 A * | 10/2000 | Trapp et al. | | 606/144 |
| 6,135,385 A * | 10/2000 | Martinez de Lahidalga | | 242/588.3 |
| 6,506,197 B1 * | 1/2003 | Rollero et al. | | 606/148 |
| 6,972,027 B2 | 12/2005 | Fallin et al. | | |
| 7,153,312 B1 | 12/2006 | Torrie et al. | | |
| 7,744,611 B2 * | 6/2010 | Nguyen et al. | | 606/151 |
| 7,875,042 B2 * | 1/2011 | Martin et al. | | 606/144 |
| 7,879,048 B2 | 2/2011 | Bain et al. | | |
| 7,905,904 B2 | 3/2011 | Stone et al. | | |
| 7,976,555 B2 * | 7/2011 | Meade et al. | | 606/148 |
| 8,210,085 B2 * | 7/2012 | Lindh et al. | | 87/34 |
| 8,545,535 B2 * | 10/2013 | Hirotsuka et al. | | 606/232 |
| 8,597,327 B2 * | 12/2013 | Stone et al. | | 606/228 |
| 8,828,054 B2 * | 9/2014 | Caborn et al. | | 606/232 |
| 2002/0151891 A1 * | 10/2002 | Glenn et al. | | 606/53 |
| 2003/0149447 A1 * | 8/2003 | Morency et al. | | 606/228 |
| 2004/0116963 A1 * | 6/2004 | Lattouf | | 606/224 |
| 2007/0038249 A1 * | 2/2007 | Kolster | | 606/228 |
| 2007/0100352 A1 * | 5/2007 | Deffenbaugh et al. | | 606/104 |
| 2007/0203508 A1 | 8/2007 | White et al. | | |
| 2007/0235359 A1 * | 10/2007 | Ruffieux et al. | | 206/339 |
| 2007/0276494 A1 * | 11/2007 | Ferree | | 623/17.11 |
| 2008/0177302 A1 * | 7/2008 | Shurnas | | 606/228 |
| 2011/0178536 A1 * | 7/2011 | Kostrzewski | | 606/144 |
| 2013/0026053 A1 * | 1/2013 | Chowaniec et al. | | 206/63.3 |

\* cited by examiner

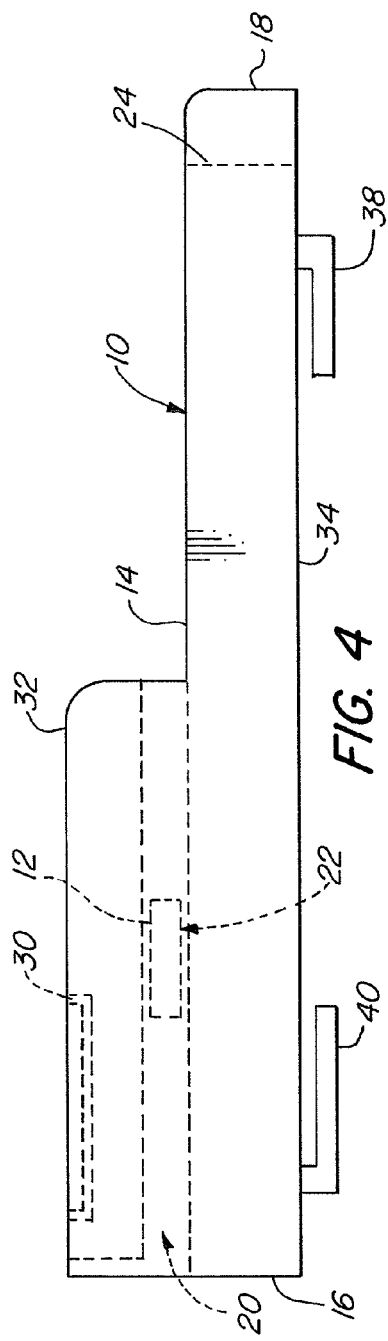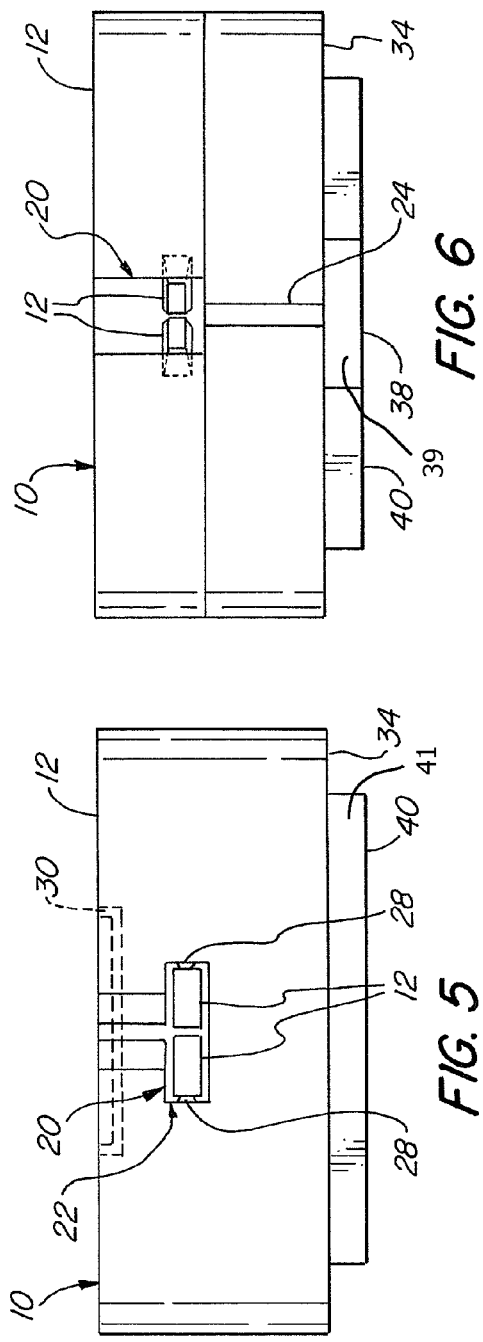

SUTURE CARTRIDGE FOR MENISCAL REPAIR

FIELD OF THE INVENTION

The present invention relates to suture holders, specifically, suture holders used in soft tissue repair as well as delivery devices and methods for using such holders, to a cartridge for releasably holding a suture holder loaded with a suture, and to kits comprising at least one suture holder, a cartridge for releasably holding at least one suture holder, and a suture.

BACKGROUND OF THE INVENTION

When a soft tissue, or a portion of a tissue, such as muscle, ligament, or cartilage, tears, surgery to repair the detached soft tissue is often required. The goal of such surgery is to suture the torn portion of the tissue to thereby repair the tear and reconstitute the tissue back to its original status. Traditionally, repair was accomplished by sewing the tissue together with two needles and a suture, then tying knots to secure the suture within the tissue. To simplify the wound closure procedure and to improve fixation, various types of suture anchors have been developed, such as those described in U.S. Pat. No. 7,153,312 B1 to Torrie et al. and U.S. Pat. No. 6,972,027 B2 to Fallin et al.

Several devices are also known for the delivery of suture anchors. Both Fallin et al. and Torrie et al. disclose delivery devices in which two or more suture anchors are delivered via a single needle and single pusher mechanism. U.S. Pat. No. 7,905,904 to Stone et al. discloses a delivery device having separate needles and pushers for delivering each of two implants.

Difficulty often arises when preparing the suture anchors for a surgical procedure. The anchors themselves are very small in size and are therefore cumbersome to handle, yet must be loaded in a specific orientation on the delivery device. In addition, properly threading the suture through the small anchors requires significant dexterity. On top of this, it is critical that all of these tasks be completed without causing knots or tangles in the suture, which would interfere with the proper implantation of the anchors. What's more, if the suture, anchors, and delivery device are all supplied separately, the surgeon must take time to find and retrieve each item individually to prepare for the surgical procedure.

U.S. Pat. No. 5,843,084 to Hart discloses a surgical fastening system for repairing tissue, including a surgical fastener and an installation tool for deploying the fastener. The surgical fastener may be removably attached to a grip for aiding in manipulation of the fastener during manufacture. The surgical fastener and grip may be packaged in a holder at the time of manufacture. The holder includes a plurality of recesses and openings for receiving the fastener and grip. An opening is also provided in the holder for permitting the installation tool to enter the holder and to engage, and then withdraw, the surgical fastener from the holder. (See Col. 9, ll. 39-59). However, as the surgical fasteners disclosed in Hart et al. do not employ sutures, the holder does not provide a means for securing a length of suture thereon.

U.S. Pat. No. 5,741,300 to Li discloses a cartridge for holding a generally cylindrical surgical fastener in position for ease of handling. The cartridge includes a holder with a gripping portion for the user to grasp, a surface for fixing the surgical fastener in position on the holder and a threading loop extending from the holder for extending through an aperture in the surgical fastener. The cartridge is generally E-shaped with two recesses and three prongs, two of which have cup-shaped portions for receiving suture anchor. The threading loop is provided as a looped spring wire having two ends which are secured in a region on the cartridge. In use, the surgeon threads a suture through the loop. When the suture anchor is then removed from the cartridge, a loop of the suture will then be threaded through the bore in the anchor. (See FIG. 7). The suture anchor can then be engaged with an insertion tool for implanting the threaded anchor into a bone. The cartridge of Li, however, does not have a means for securing a portion of the suture thereon.

What is desired, therefore, is a device, such as a cartridge, for releasably holding at least one suture anchor and a suture threaded therethrough in a manner to be easily loaded onto a delivery device and in such a way that any extra length of suture can be secured on the cartridge and prevented from tangling. Further, what is desired is a kit, including a cartridge releasably holding at least one suture anchor preloaded with a suture.

SUMMARY OF THE INVENTION

Accordingly, it is an object of the present invention to provide a cartridge for holding a suture anchor, comprising a body including a holder assembly adapted to releasably hold at least one suture anchor; a passage extending from a side of said body to said holder assembly; and a spool, which may include two posts, adapted to releasably wind a portion of a suture therearound. In one embodiment, the holder assembly is adapted to releasably accept two suture anchors. In some embodiments, the passage in said body is horizontally aligned with the holder assembly. In further embodiments, the passage is vertically aligned with the holder assembly. The holder assembly may include at least one tab releasably connected to said at least one suture anchor. Each of the two posts of the spool, one of which may be located at a distal end of said body and the other of which may be located at a proximal end of the body, may have an outwardly-facing generally rounded surface. In another embodiment, the cartridge may further include a frame on said body adapted to hold a portion of said suture in a loop, which may be a recess having essentially in the shape of a loop. A longitudinal slit adapted to receive at least a portion of a suture may also be provided in the distal end of the body of the cartridge.

A further object of the invention is to provide a suture anchor kit comprising two suture anchors connected by a suture; and a cartridge, releasably holding said two suture anchors; said cartridge including a spool adapted to releasably wind a portion of a suture therearound. The suture cartridge may further include at least one tab releasably connected to each of said at two suture anchors. In a further embodiment, the cartridge includes a frame adapted to hold a portion of said suture extending between said two suture anchors in the shape of a loop, which may be provided as a recess in said cartridge. The suture anchor kit may also include a delivery device adapted to implant said suture anchors into tissue.

BRIEF DESCRIPTION OF THE DRAWINGS

FIG. 4 is a side view of the cartridge of FIG. 1.

FIG. 5 is a proximal end view of the cartridge of FIG. 1.

FIG. 6 is a distal end view of the cartridge of FIG. 1.

DETAILED DESCRIPTION OF THE INVENTION

Figure 1:
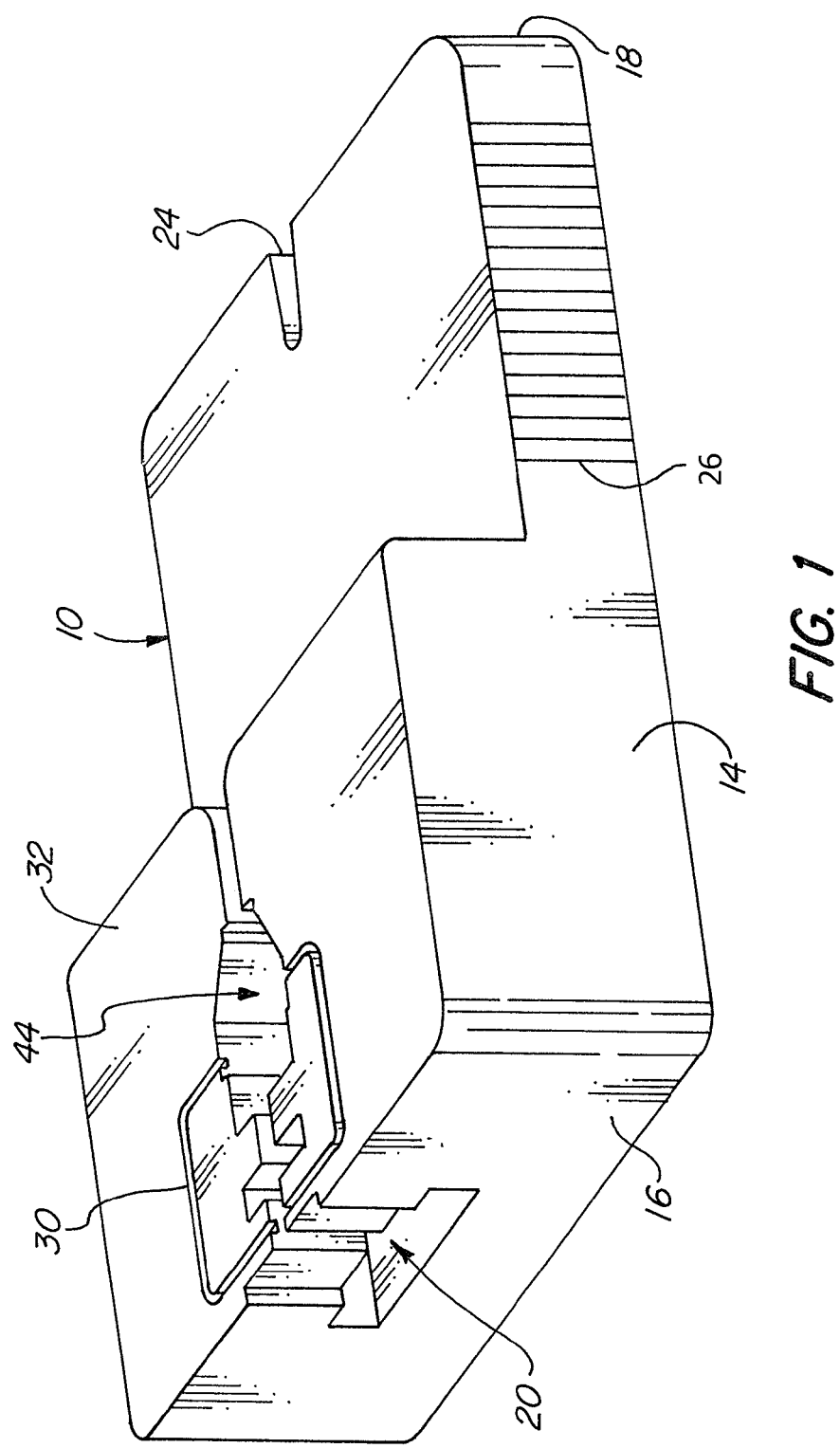
FIG. 1 is a perspective view of an embodiment of the cartridge of the present invention.

An embodiment of the cartridge 10 for releasably holding at least one suture anchor 12 of the present invention is shown in FIG. 1. The cartridge 10 comprises a body 14 having proximal 16 and distal 18 faces. A passage 20 extends from the proximal face 16 of the body 14 to a holder assembly 22, shown in FIG. 2. A longitudinal slit 24 for passing a suture may also be provided in the distal face 18 of the body 14, the utility of which will be explained further below. The passage 20 may be shaped to receive the distal end of a delivery device (not shown) for capturing the at least one suture anchor 12. Grips 26 may also be provided on either side of the body 14 to aid in manipulation of the cartridge 10. The cartridge 10 may be made of any suitable material, including, for example a lightweight molded plastic.

Generally, in operation, the cartridge 10 acts to releasably hold at least one suture anchor 12 to aid in one or more of manufacture, threading of the anchor with a suture, packaging, transport and handling prior to use. As discussed above, the suture anchors are very small in size and, therefore difficulty in manipulating the suture anchor(s) during these actions can be greatly reduced when the suture anchors are secured within the cartridge. Moreover, not only does the cartridge 10 aid in manipulation of the suture anchor(s), but it also maintains the proper positioning of a suture and the suture anchor(s) during threading of the suture therein and also in loading of the anchors and suture on a delivery device. Typically, the sutures must be positioned in a particular orientation when loaded on to the delivery device for use in a surgical procedure. The cartridge 10, along with the at least one suture anchor 12 may be manufactured at the same time, or, alternatively, they may be manufactured separately and the at least one anchor 12 may be subsequently inserted into the cartridge 10.

Figure 2:
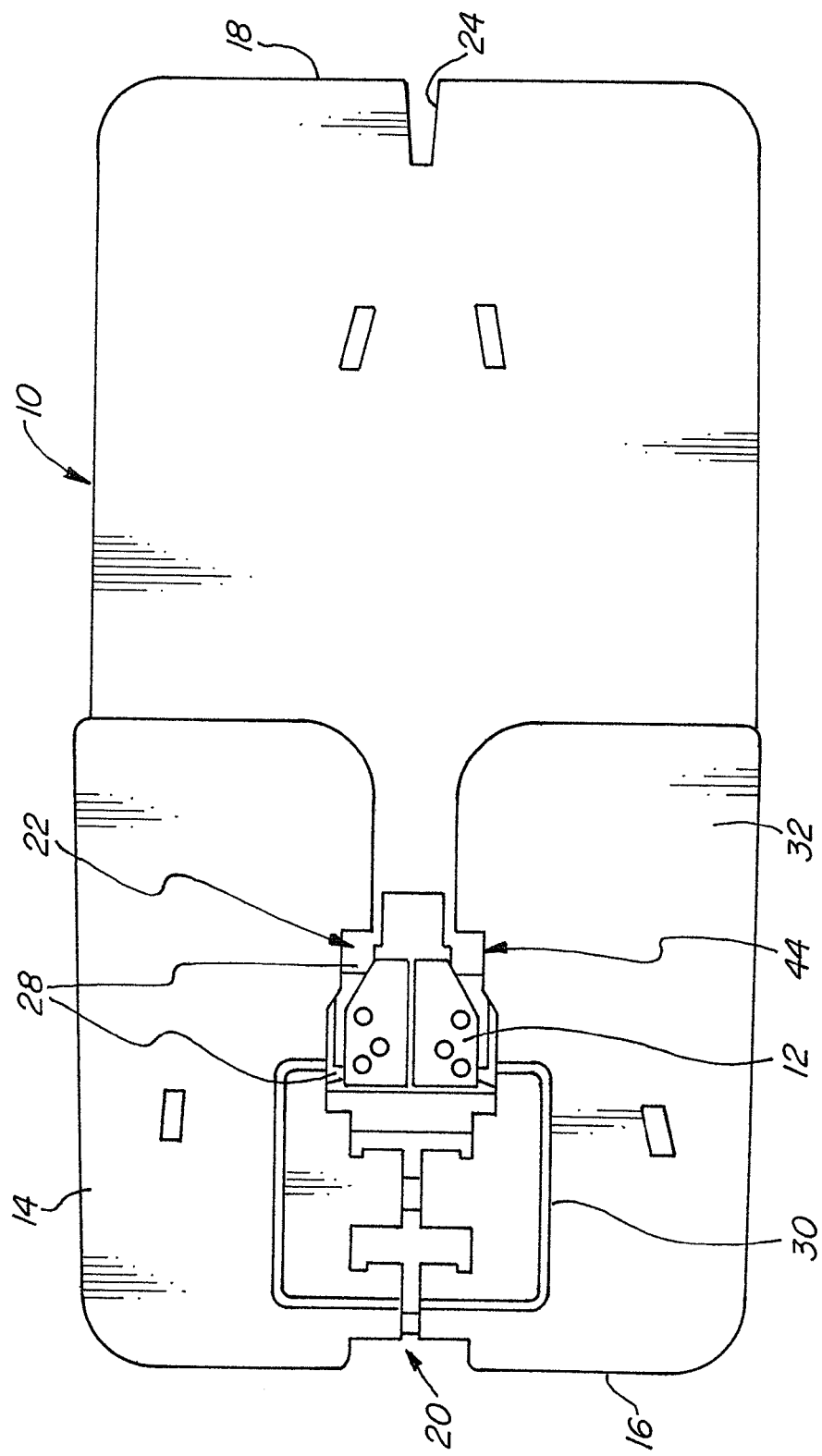
FIG. 2 is a top view of the cartridge of FIG. 1.

Turning to FIG. 2, the holder assembly 22 comprises at least one tab 28 connecting the at least one anchor 12 to the body 14. In one embodiment, the at least one tab 28 is designed to be self-breaking, meaning that when sufficient force is applied to the suture anchors, the bond between the tabs 28 and the anchors 12 will break, releasing the anchors 12 from the body 14. However, the material and construction of the at least one tab 28, and the strength of the bond between the anchor 12 and the tab 28, should be chosen such that the bond does not break during manufacture, threading of the anchor with a suture, packaging, transport and handling prior to use. In another embodiment, the at least one tab 28 holds the at least one anchor 12 to the body 14 by a friction fit. The at least one tab 28 may be made from the same material as the body 14. In one embodiment, the holder assembly 22 includes two tabs 28 per suture anchor 12.

A frame 30 may be provided in the top surface 32 of the body 14 for holding a portion of a suture (not shown) threaded between two suture anchors 12 in a loop, the utility of which will be explained in detail below. In many surgical procedures utilizing two suture anchors 12 connected by a suture, it is necessary to have a loop or length of suture between the two anchors 12. The frame 30 may be provided as an indentation in the top surface 32 of the body 14, or as any other suitable structure for holding a loop of suture, including a protrusion of the same shape or one or more pegs.

Figure 3:
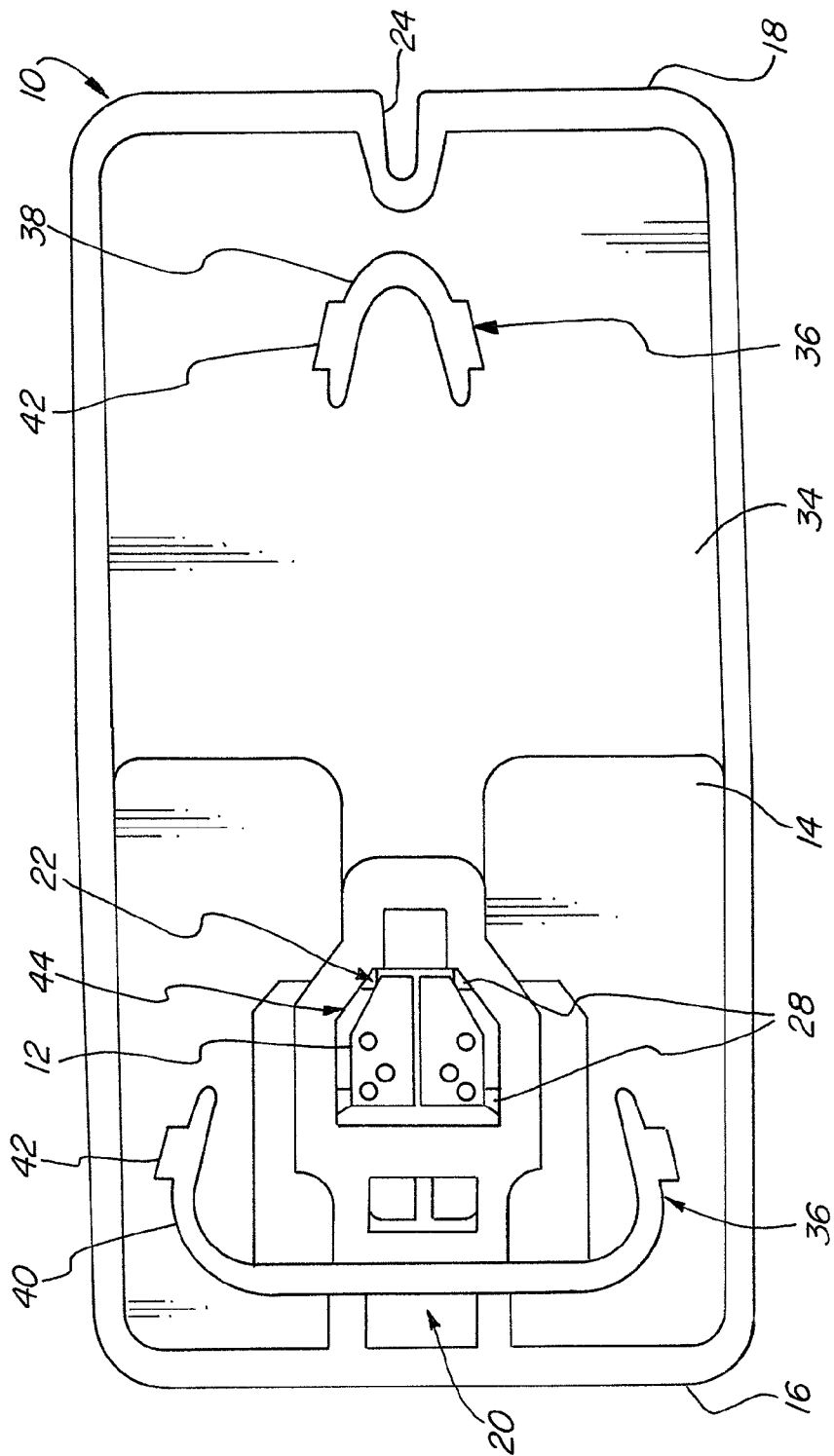
FIG. 3 is a bottom view of the cartridge of FIG. 1.

As shown in FIG. 3, spool 36 extends from the bottom surface 34 of the body 14 for releasably winding a portion of a suture therearound. The spool 36 may include a distal post 38 and a proximal post 40. The posts 38,40 may be provided in any number of appropriate shapes, including simple dowels. In the embodiment depicted in FIG. 3, the outward facing surfaces 39,41 of posts 38,40 are both generally rounded. The posts 38,40 may also be provided with at least one flange 42 extending therefrom to prevent the suture wrapped therearound from sliding off of the post.

The cartridge 10 may also be provided with an access passage 44, extending from the top surface 32 through to the bottom surface 34 of the body 14. This passage 44 permits a suture to be threaded through the at least one suture anchor 12 while it is secured in the cartridge 10.

The holder assembly 22 is positioned in communication with the passage 20 such that a delivery device may be introduced into the cartridge through the passage 20 and capture the at least one suture anchor 12 from the holder assembly 22. In one embodiment, the holder assembly 22 is in horizontal alignment with the passage 20. This can be seen from FIG. 4. In this embodiment, the holder assembly 22 and the passage 20 generally lie within the same horizontal plane and, therefore, a delivery device may be introduced essentially horizontally into the passage 20 for capturing the at least one suture anchor 12. In a further embodiment, the holder assembly 22 is in vertical alignment with the passage 20, which can be seen from FIGS. 5 and 6.

Figure 7:
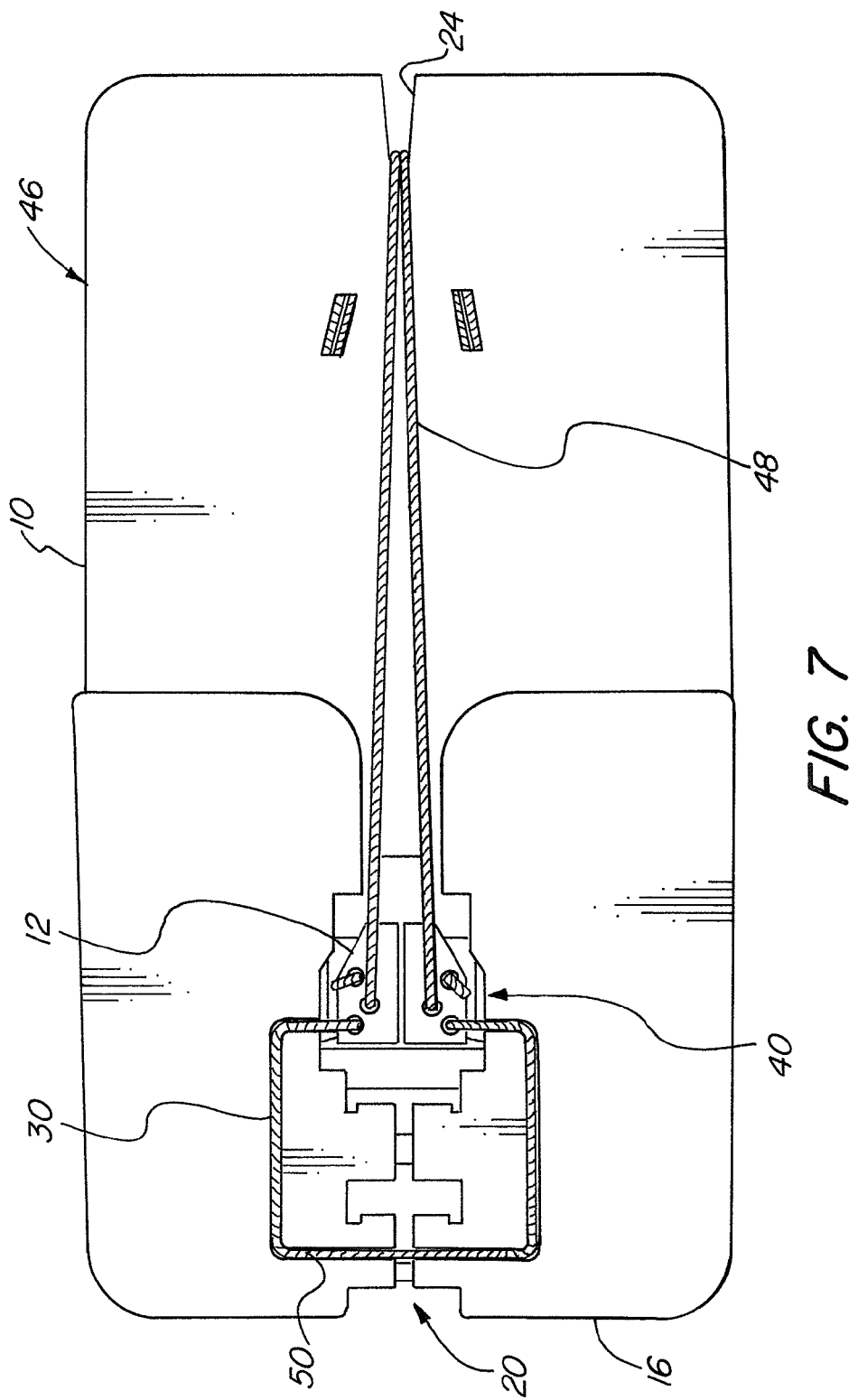
FIG. 7 is a top view of an embodiment of and embodiment of the kit of the present invention, including a cartridge, suture anchors and a suture.
Figure 8:
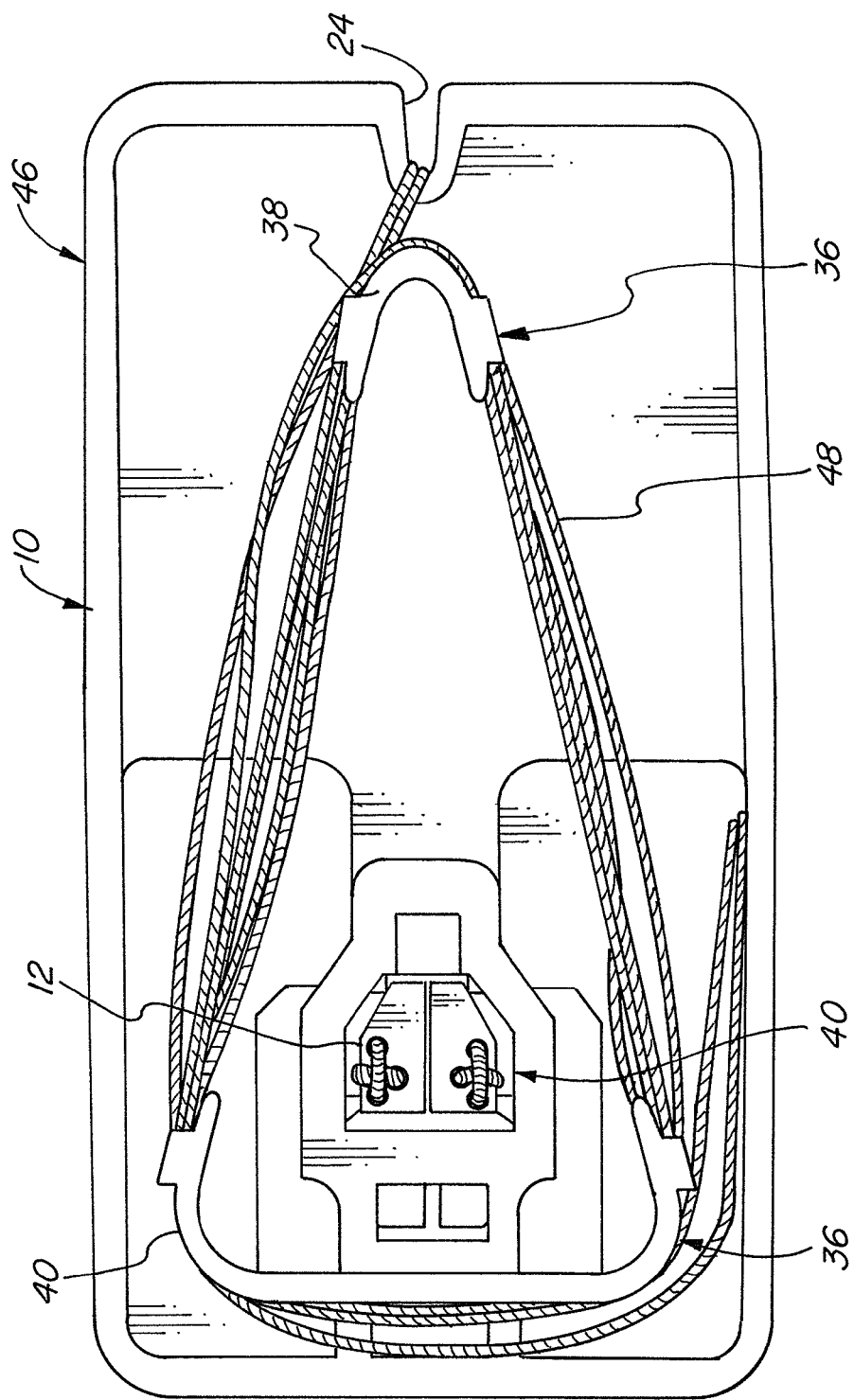
FIG. 8 is a bottom view of an embodiment of and embodiment of the kit of the present invention, including a cartridge, suture anchors and a suture.

FIGS. 6 and 7 depict a kit 46 comprising a cartridge 10, at least one suture anchor 12 and a suture 48. In the particular embodiment shown in these Figures, the kit 46 includes two suture anchors 12. The suture 48 is threaded through the anchors 12 with a connecting portion 50 held in the shape of a loop by frame 30. The free ends of the suture 48 then pass from the top surface 32 to the bottom surface 34 of the body 14. In this embodiment, the suture passes through slot 24, which prevents the suture 48 from sliding along the distal face 18 of the body 14. The free ends of the suture are secured to the bottom surface 34 of the body by being wrapped around the spool 36, which, in this embodiment includes two posts 38, 40. The entire kit 46, with the cartridge 10 and anchors 12 with suture 48 threaded therein may be packaged in a sterile bag (not shown). As is clear from the foregoing discussion, this kit provides great convenience to the surgeon by having all of the necessary supplies to perform a surgical procedure together in one sterile package, by providing the suture anchors 12 preloaded with suture, and by providing a cartridge for easily manipulating the anchors while they are loaded onto a delivery device.

Figure 9:
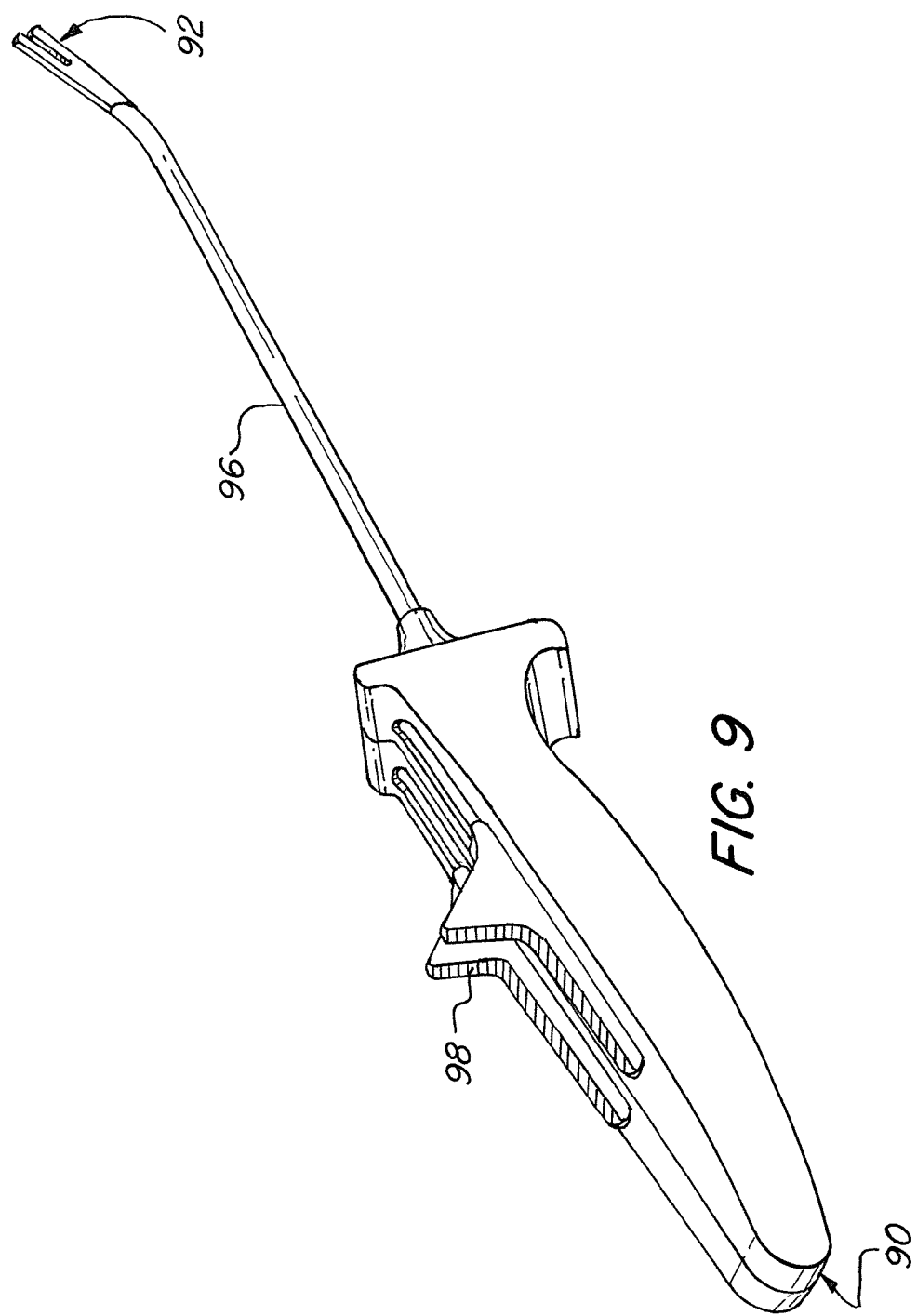
FIG. 9 is a perspective view of an exemplary embodiment of a delivery device.
Figure 10:
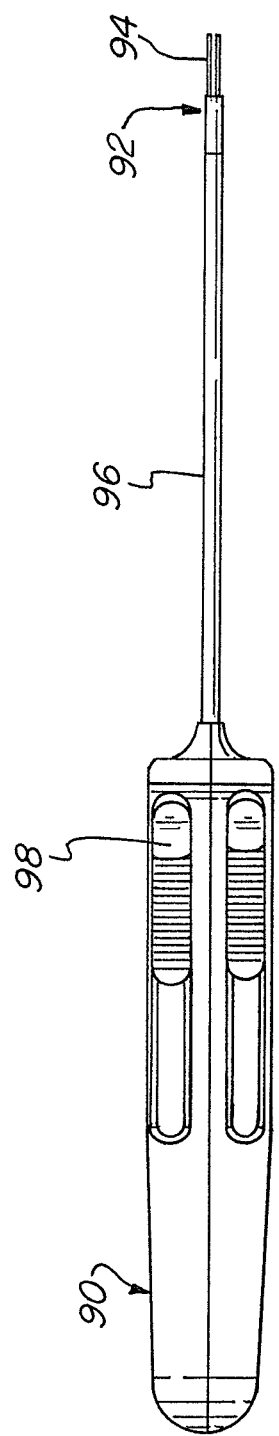
FIG. 10 is a top view of an exemplary embodiment of a delivery device.

One exemplary delivery device 90 for use with the kit 46 is depicted in FIG. 9. This exemplary delivery device 90 has a distal end 92 for receiving the at least one suture anchor 12. At least one delivery needle 94 is slidably disposed in the shaft 96 of the delivery device 90 and is actuated by at least one pusher mechanism 98. The delivery device depicted in FIGS. 9-15 is exemplary in nature and any suitable delivery device may be used in connection with the kit 46 of the present invention, including, without limitation a delivery device that does not have individually actuated needles.

Figure 11:
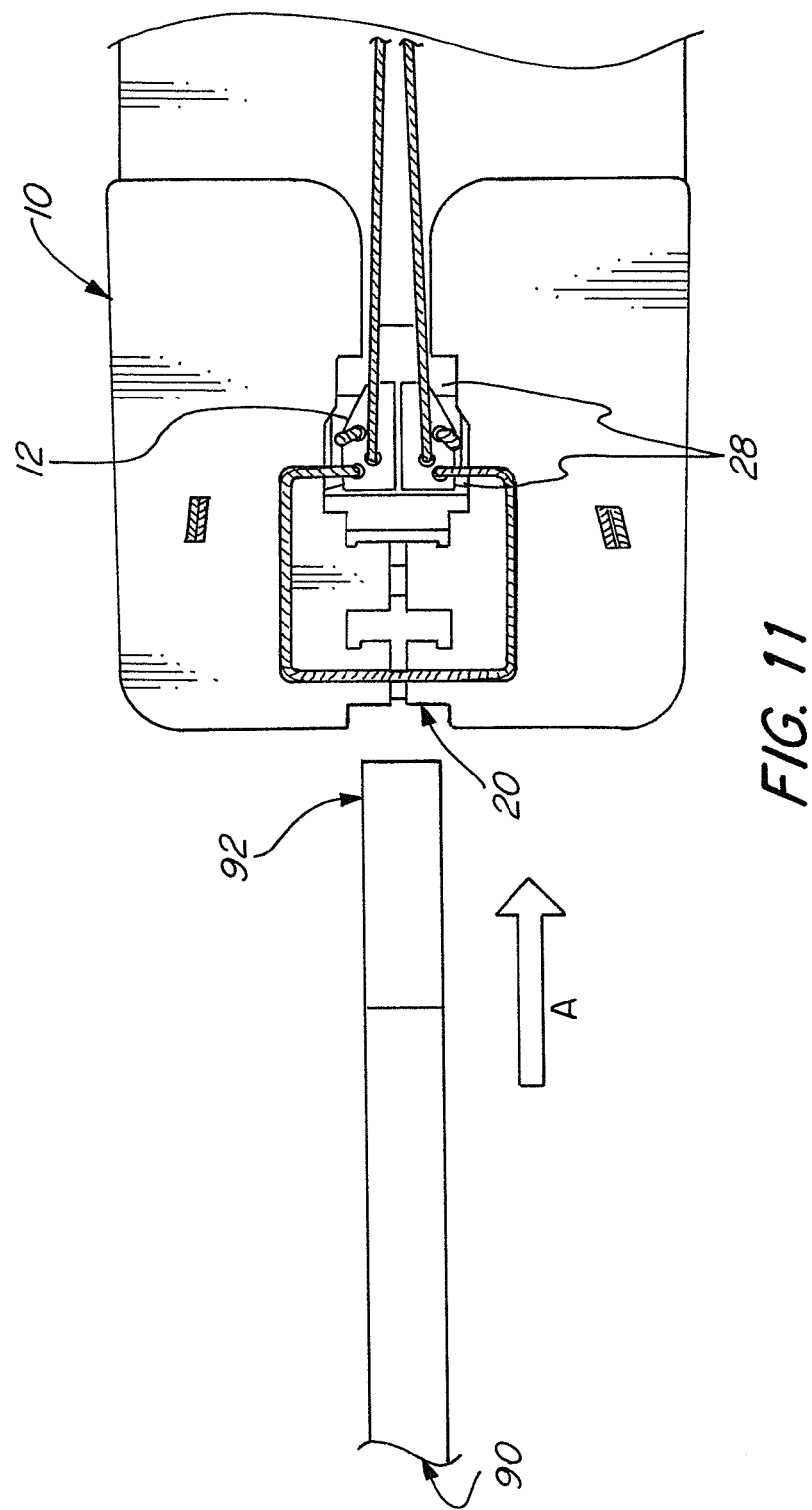
FIG. 11 is a top view of an embodiment of the cartridge of the present invention and a portion of a delivery device moving towards the proximal end of the cartridge.
Figure 12:
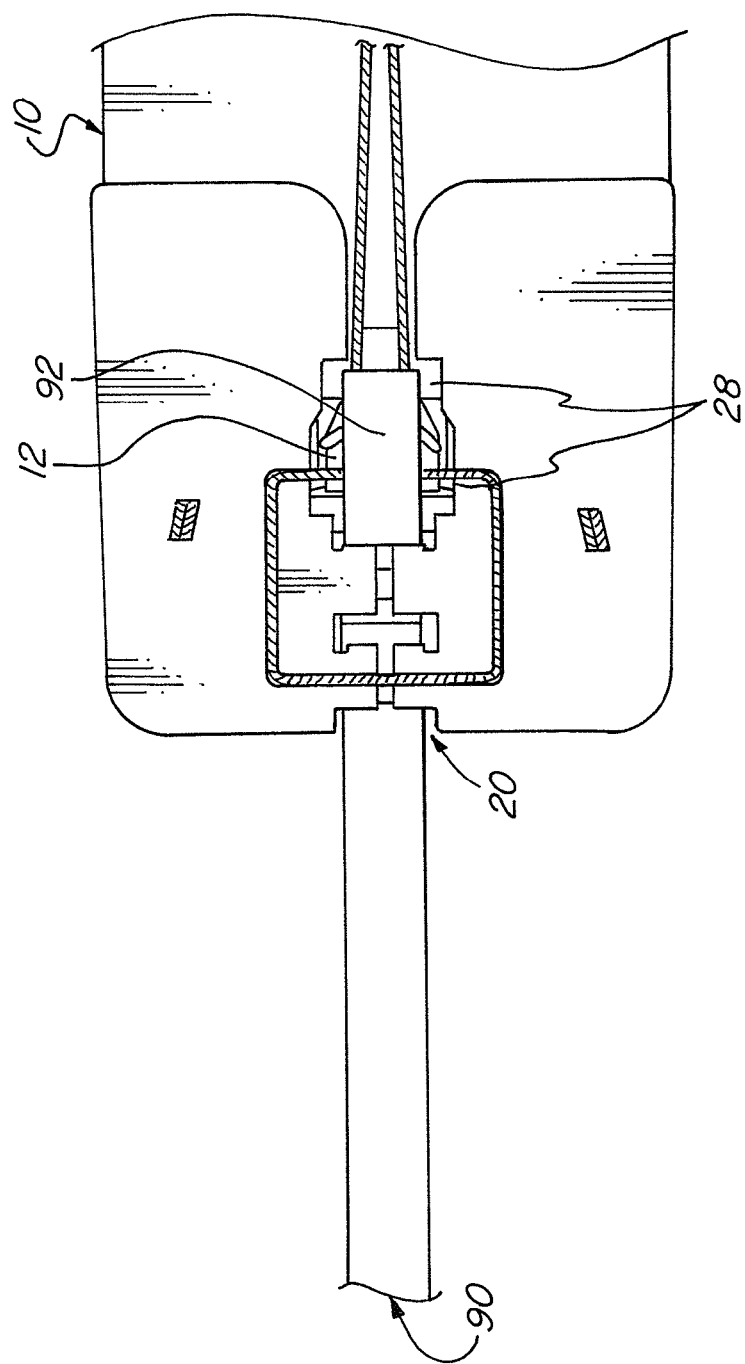
FIG. 12 is a top view of an embodiment of the cartridge of the present invention and a portion of a delivery inserted into the proximal end of the cartridge.
Figure 13:
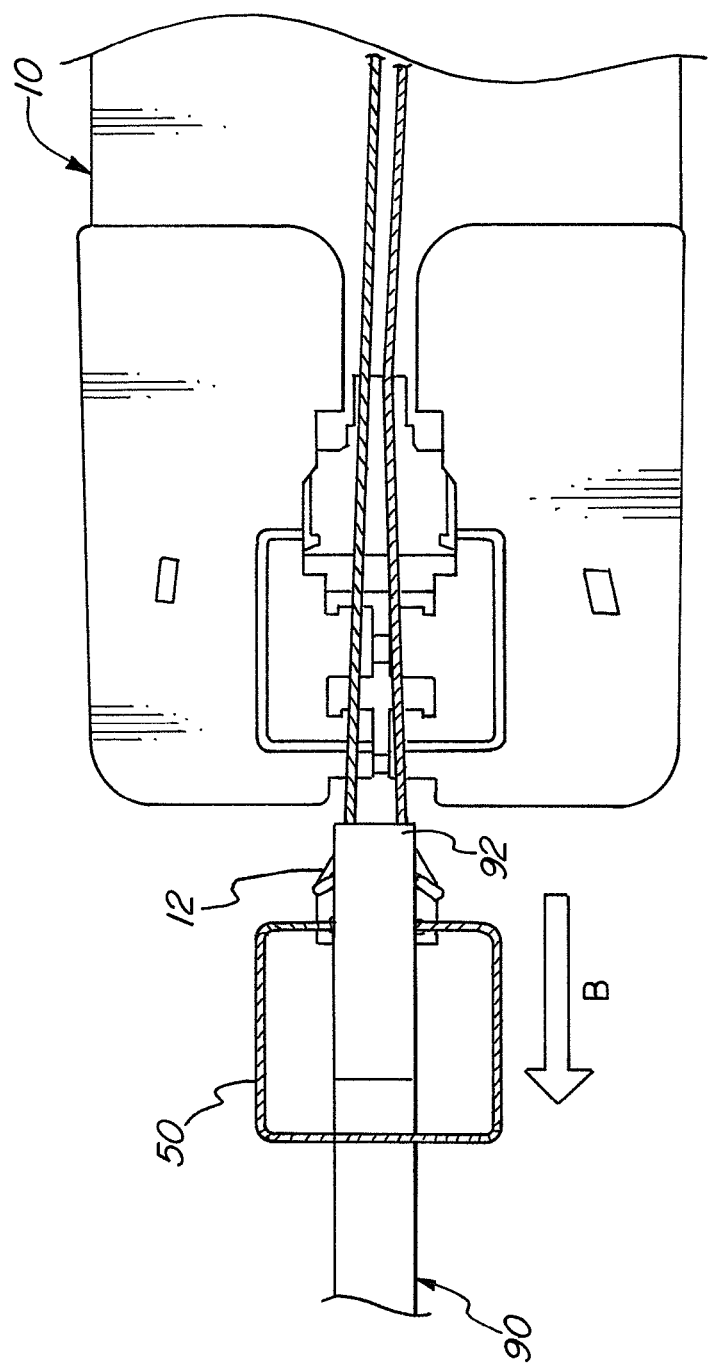
FIG. 13 is a top view of an embodiment of the cartridge of the present invention and a portion of a delivery device moving away from the proximal end of the cartridge.
Figure 14:
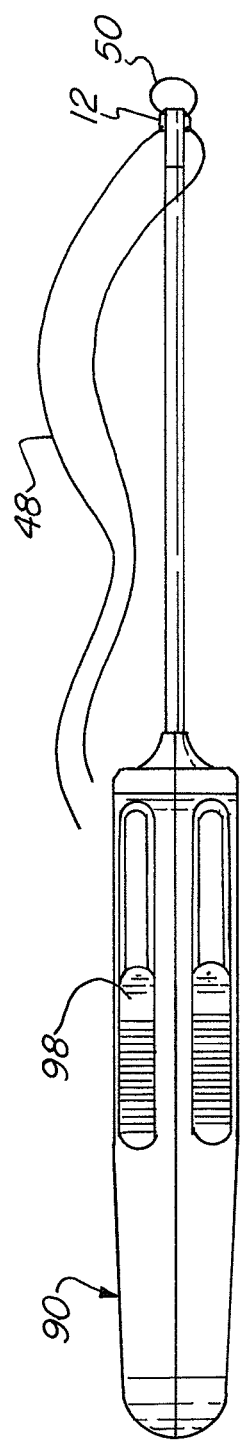
FIG. 14 is a top view of an exemplary embodiment of a delivery device after having been loaded with two suture anchors and a suture.
Figure 15:
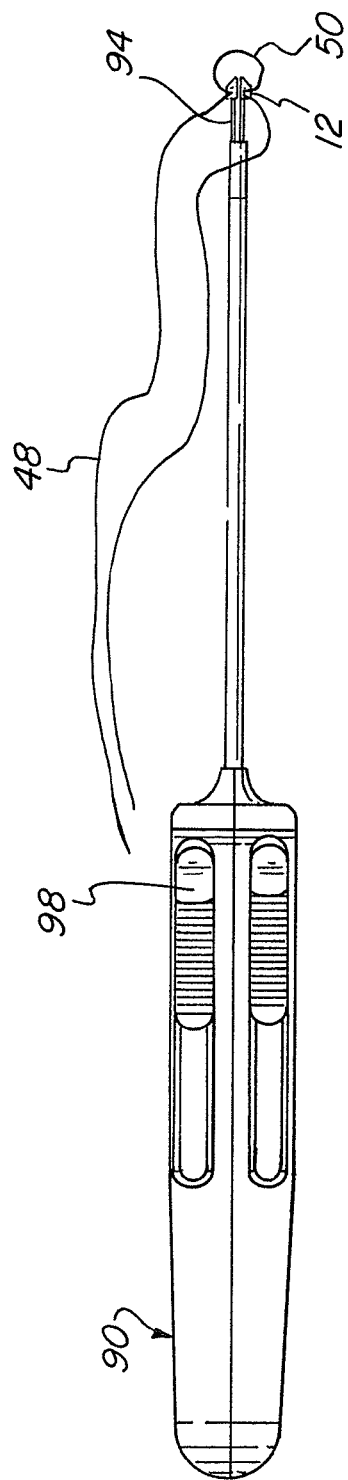
FIG. 15 is a top view of an exemplary embodiment of a delivery device after having been loaded with two suture anchors and a suture.

In operation, the distal end 92 of a delivery device 90 is introduced into the cartridge 10 via passage 20 in the direction of arrow A, as shown in FIG. 11. Delivery device 90 is moved in a distal direction until reaching the at least one suture anchor 12 releasably held in the holder assembly 22, as shown in FIG. 12. The at least one suture anchor 12 is then loaded onto the delivery device. In this embodiment, the at least one delivery needle 94 will be actuated via pusher mechanism 98 and received in a longitudinal passage in the at least one suture anchor 12. A force is then applied to the at least one suture anchor 12, either merely by pulling the delivery device in the direction of arrow B or by a slight twisting of the delivery device or the cartridge, to break the bond between the at least one suture anchor 12 and the at least one tab 28. The entire delivery device 90, with the threaded suture anchors 12 loaded therein, as illustrated in FIG. 14, may be removed from the cartridge 10 in the direction of arrow B and the free ends of the suture 48 may be unwound from the spool 36. FIG. 15 illustrates the two delivery needles 94 of the exemplary delivery device 90 with two threaded suture anchors 12 loaded thereon extended from the distal end of the delivery device 90 via pusher mechanisms 98.

Figure 16A:
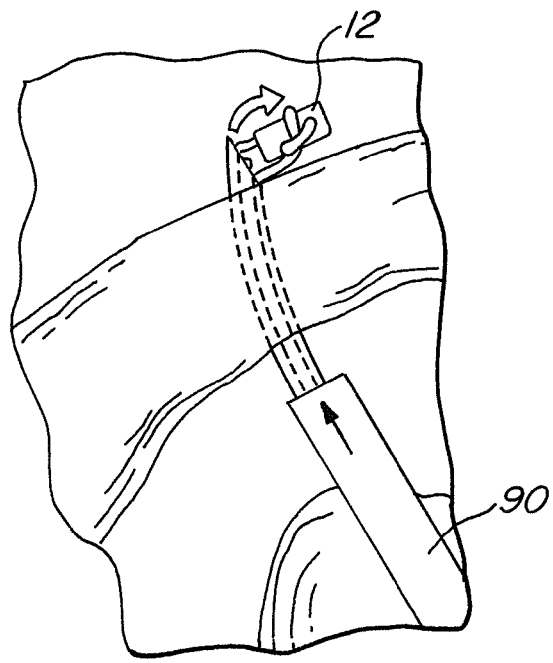
FIGS. 16A and 16B illustrate a delivery device and suture anchors being used to repair a tear in tissue.
Figure 16B:
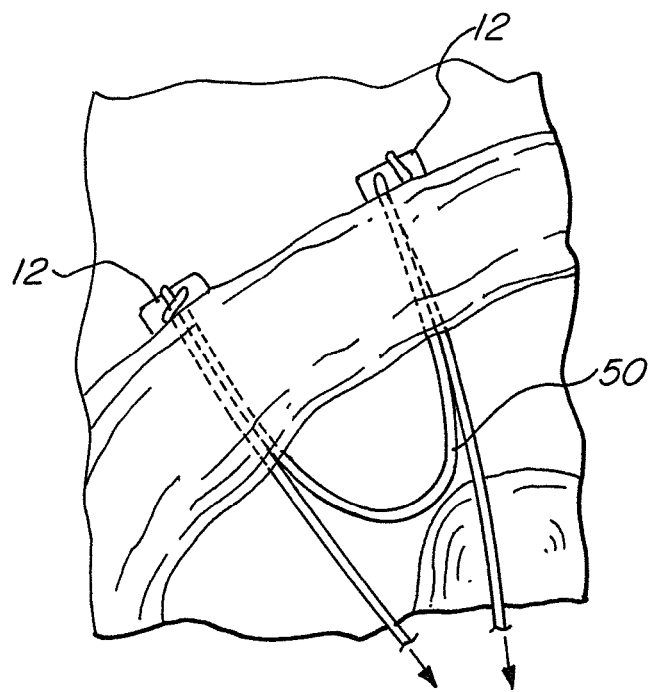

FIGS. 16A and 16B illustrate two suture anchors 12 being used in an exemplary fashion to repair a tear in tissue. Generally, the threaded anchors 12 are implanted into tissue one after another via a delivery device 90 such that the connecting portion 50 of the suture is sewn across a tear in tissue. For this reason, it is important to provide a means on the cartridge 10 to preserve a connecting portion of suture having a certain length.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A cartridge for holding a suture anchor, comprising:
   at least one suture anchor;
   a body including a holder assembly configured to releasably hold the at least one suture anchor, the at least one suture anchor having a suture threaded there through, the body having a proximal end and a distal end;
   a passage extending from the proximal end of said body to said holder assembly; and
   a spool configured to releasably wind a portion of a suture therearound, the spool located distally to said passage and to said holder assembly along an axis extending from the proximal end to the distal end of the body;
   the cartridge receiving a delivery device via the passage to load the at least one suture anchor onto the delivery device;
   a longitudinal slit in the distal end of said body configured to receive at least a portion of a suture, said distal end located opposite an end of said body where the delivery device is inserted into the passage.

2. The cartridge of claim 1 wherein said holder assembly is configured to releasably accept two suture anchors.

3. The cartridge of claim 1 wherein said holder assembly comprises at least one tab releasably connected to said at least one suture anchor.

4. The cartridge of claim 1 wherein said spool comprises two posts.

5. The cartridge of claim 4 wherein each of said two posts has a generally rounded surface.

6. The cartridge of claim 1 wherein said passage is horizontally aligned with said holder assembly.

7. The cartridge of claim 1 wherein said passage is vertically aligned with said holder assembly.

8. The cartridge of claim 1 further comprising a needle affixed to the delivery device.

9. The cartridge of claim 8 wherein the needle is slidably disposed on the delivery device.

10. The cartridge of claim 1, further comprising an access passage extending from a top surface to a bottom surface of the body, the access passage configured to permit the suture to be threaded through the at least one suture anchor while it is secured in the cartridge.

11. The cartridge of claim 3, wherein the at least one tab of the holder assembly provides a bond between the suture anchor and the body, the tab configured such that the bond breaks when a sufficient force is applied to the suture anchor by the delivery device when loading the suture anchor on the delivery device.

12. The cartridge of claim 1, wherein the at least one tab holds the at least one suture anchor to the body by a friction fit.

13. A suture anchor kit, comprising:
   two suture anchors connected by a suture; and
   a cartridge releasably holding said two suture anchors, the cartridge including a passage and a spool configured to releasably wind a portion of the suture therearound, the cartridge receiving a delivery device via the passage to load at least one of the two suture anchors onto the delivery device; and
   at least one needle affixed to and slidably disposed on the delivery device, the at least one needle actuated by a mechanism which slides the needle.

14. The suture anchor kit of claim 13 wherein said cartridge further comprises at least one tab releasably connected to each of said at two suture anchors.

15. The suture anchor kit of claim 13 wherein said cartridge further includes a frame configured to hold a portion of said suture extending between said two suture anchors in the shape of a loop.

16. The suture anchor kit of claim 15 wherein said frame comprises a recess in said cartridge.

17. The suture anchor kit of claim 15 further comprising a delivery device configured to implant said suture anchors into tissue.

18. The suture anchor kit of claim 13 wherein said at least one needle comprises two needles, each of the two suture anchors loaded onto one of the two needles when the two suture anchors are loaded onto the delivery device.

19. The suture anchor kit of claim of claim 14, wherein the at least one tab of the holder assembly provides a bond between the two suture anchors and the body, the tab configured such that the bond breaks when a sufficient force is applied to the two suture anchors by the delivery device when loading the two suture anchors on the delivery device.

20. A cartridge for holding a suture anchor, comprising:
a body including a holder assembly configured to releasably hold at least one suture anchor, the at least one suture anchor having a suture threaded there through, the body having a proximal end and a distal end;
a passage extending from the proximal end of said body to said holder assembly; and
a spool configured to releasably wind a portion of a suture therearound, the spool located distally to said passage and to said holder assembly along an axis extending from the proximal end to the distal end of the body;
a frame on said body configured to hold a portion of said suture in a loop, said frame comprises a recess in said body;
the cartridge receiving a delivery device via the passage to load the at least one suture anchor onto the delivery device;
wherein the holder assembly comprises at least one tab providing a bond between the suture anchor and the body, the tab configured such that the bond breaks when a sufficient force is applied to the suture anchor by the delivery device when loading the suture anchor on the delivery device.

21. The cartridge of claim 20 wherein said recess is essentially in the shape of a loop.

* * * * *